United States Patent [19]

Hall

[11] Patent Number: 4,935,015
[45] Date of Patent: Jun. 19, 1990

[54] SYRINGE APPARATUS WITH RETRACTABLE NEEDLE

[76] Inventor: John E. Hall, 5751 Richards Cir., Shawnee, Kans. 66216

[21] Appl. No.: 284,195

[22] Filed: Dec. 14, 1988

[51] Int. Cl.$^5$ .............................................. A61M 5/32
[52] U.S. Cl. .................................... 604/195; 604/241
[58] Field of Search ............... 604/195, 198, 110, 263, 604/192, 187, 194, 193, 197, 240, 241

[56] References Cited

U.S. PATENT DOCUMENTS

| | | |
|---|---|---|
| 2,688,325 | 9/1954 | Lockhart . |
| 2,888,923 | 6/1295 | DaCunha Reis . |
| 3,354,882 | 11/1967 | Coanda . |
| 3,487,834 | 1/1970 | Smith, Jr. et al. . |
| 3,527,216 | 9/1970 | Snyder . |
| 3,890,971 | 6/1975 | Leeson et al. . |
| 4,026,287 | 5/1977 | Haller . |
| 4,425,120 | 1/1984 | Sampson et al. . |
| 4,493,703 | 1/1985 | Butterfield . |
| 4,507,117 | 3/1985 | Vining et al. . |
| 4,566,844 | 1/1986 | Carpenter et al. . |
| 4,573,976 | 3/1986 | Sampson et al. . |
| 4,573,981 | 3/1986 | McFarlane . |
| 4,592,744 | 6/1986 | Jagger et al. . |
| 4,596,562 | 6/1986 | Vernon . |
| 4,610,667 | 9/1986 | Peducano et al. . |
| 4,643,200 | 2/1987 | Jennings et al. . |
| 4,650,468 | 3/1987 | Jennings, Jr. . |
| 4,655,751 | 4/1987 | Harbaugh . |
| 4,664,654 | 5/1987 | Strauss . |
| 4,666,435 | 5/1987 | Braginetz . |
| 4,675,005 | 6/1987 | DeLuccia . |
| 4,692,156 | 9/1987 | Haller ................................ 604/195 |
| 4,695,274 | 9/1987 | Fox . |
| 4,710,170 | 12/1987 | Haber et al. . |
| 4,731,059 | 3/1988 | Wanderer et al. . |
| 4,747,830 | 5/1988 | Gloyer et al. . |

Primary Examiner—John D. Yasko
Attorney, Agent, or Firm—Litman, McMahon & Brown

[57] ABSTRACT

A hydopermic needle apparatus includes a barrel having an internal chamber, a plunger mounted in said chamber and adapted to be movable both axially and rotatably within the chamber, and a needle mechanism. The barrel includes a collar at a tip thereof having an internal bore and having first and second threaded connector fittings separated by a stop within the bore. The plunger has, at one end thereof, a hub extending outwardly toward the needle mechanism. The needle mechanism includes a base with a needle extending therefrom and having an internal cavity that opens opposite the needle. The base also includes a third connector fitting adapted to mate with either of the first or second fittings within the collar. The plunger hub is adapted to snugly fit within the cavity of the needle mechanism base such that the base will frictionally engage the hub for positioning of the third connector fitting within the interior most of the first or second connector fittings and thereafter be disengageable from the cavity by axially withdrawing the plunger. The process can be reversed in order to dismount the needle mechanism from the collar and withdraw or retract the needle mechanism into the barrel chamber. A plug is provided to cap the collar, when the needle mechanism is positioned within the barrel chamber, and prevent flow of fluids or passage of the needle through the collar bore.

11 Claims, 2 Drawing Sheets

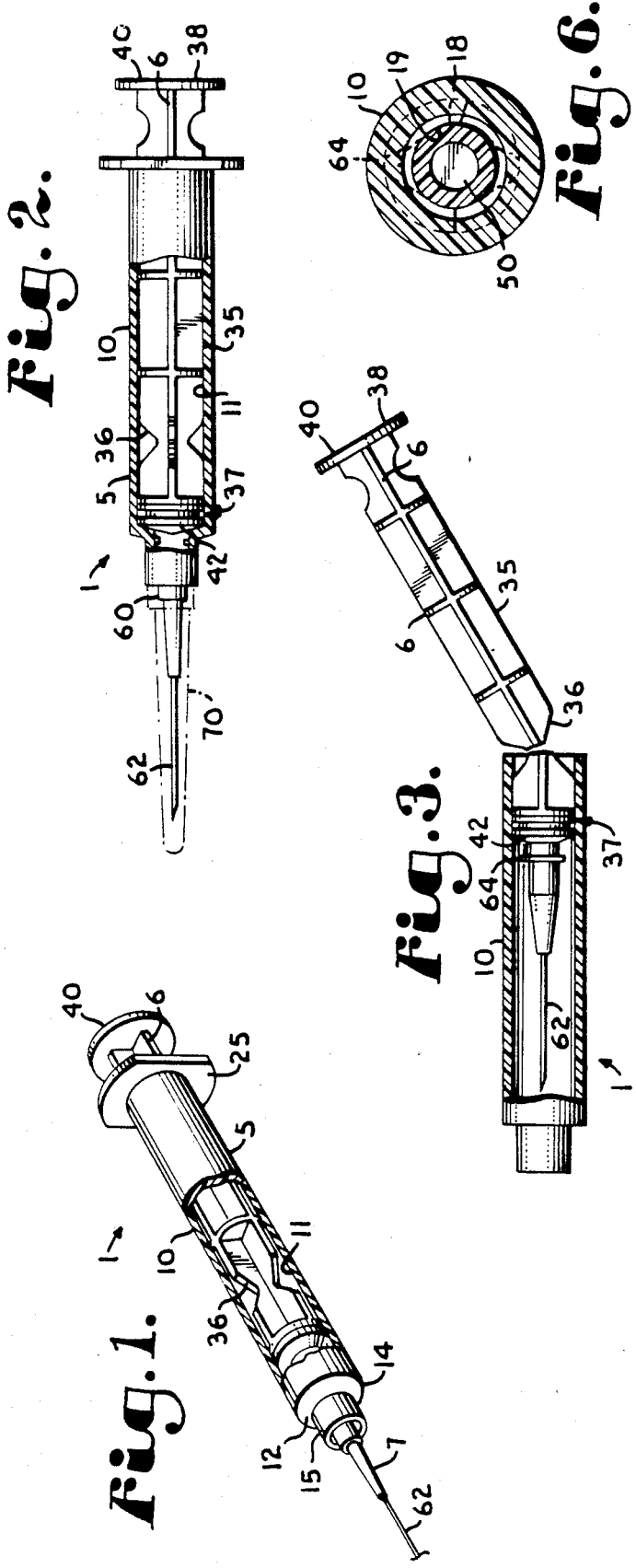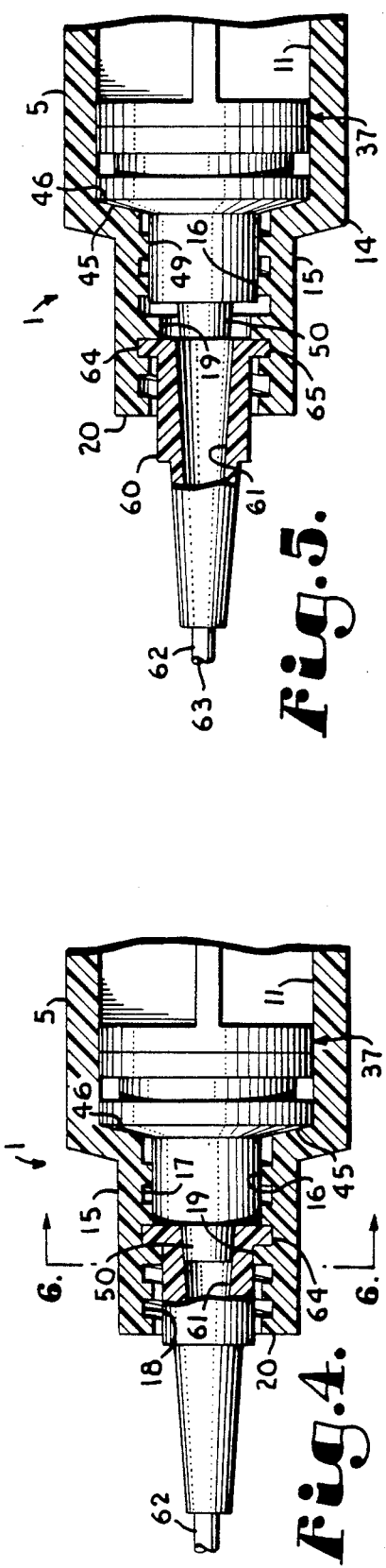

SYRINGE APPARATUS WITH RETRACTABLE NEEDLE

BACKGROUND OF THE INVENTION

The present invention relates to a disposable hypodermic syringe for use in injecting or withdrawing fluids that is adapted to prevent accidental needle sticks and to be rendered nonreusable subsequent to initial use.

In the health care field, medical practitioners such as nurses and doctors, as well as related personnel such as clean-up workers and the like, are subject to the hazard known as "needle stick". A needle stick occurs when the epidermis of a person who is not the intended subject of an injection or fluid withdrawal is punctured by a hypodermic needle, especially after the needle has been used on another person who could be contaminated with a transferable microorganism. Needle sticks may occur when health care workers attempt to recap syringes after use. This is usually due to the worker being careless in trying to guide the needle into the relatively small opening in the cap or when the worker is bumped during the capping process. Sticks also occur when a cap is dislodged from the needle during handling or when uncapped needles are encountered by cleaning persons. Used needles pose a potential threat of transfering dangerous microorganisms until fully destroyed due to such sticks.

While it is possible for a health care worker to be stuck prior to use of the needle in a patient and then have the needle pass on infectious material from the worker to the patient, needle sticks are usually most hazardous when occurring subsequent to use of the needle for injection or withdrawal of fluid from a patient carrying a communicable virus such as the hepatitis or AIDS (auto immune deficiency syndrome) causing viruses. Before the widespread incidence of AIDS, a stick was usually followed by a shot of a passive immunizing agent (immune serum globulin) to reduce the chance of contacting hepatitis. Because there is no known immuglobin or anti-serum to treat the AIDS causing viruses, preventing needle sticks with hypodermic needles contaminated with the AIDS viruses is of paramount concern. The need to prevent needle stick is heightened due to the current inability of medical practitioners or hospitals to force patients to be tested for AIDS prior to treatment or, even if tests are conducted, to be able to detect AIDS or exposure to the AIDS causing viruses during the first several months after exposure. It is foreseeable that a person receiving a needle stick may engage in conduct which would unknowingly again transmit the virus. Even where communicable diseases are not a threat, subjects of needle sticks are generally required to receive injections of immune serum globin as a precautionary measure resulting in discomfort and apprehension by the recipient as well as additional testing and cost to the responsible health care facility.

In addition to the threat of needle stick, it is known that in underdeveloped countries hypodermic syringes are often reused without proper sterilization. Also, used syringes are known to fall into the hands of illegal drug users who may pass the syringe between users and use the syringes multiple times without sterilization to inject themselves and others. The availability of operable used syringes arguably is thus a contributing cause of continued drug abuse and one key factor in the transmission of diseases by users of illegally administered drugs.

Numerous modified syringe configurations and appliances have been developed in recent years to lessen the likelihood of needle stick occurrences. Additionally, several alternative disposable syringes have been developed which may be rendered inoperable after use to combat drug abuse and the transfer of disease.

In particular, devices have been manufactured or suggested that are directed toward reducing the needle stick hazard and may be, in general, divided into two categories. First, are those devices that assist the user in resheathing or recapping the needle after use. The resheathing devices generally either provide a mechanism for replacing a detachable cap or sheath without the need for the user's hands coming into proximity to the needle point or contain a movable cylinder located concentrically about the syringe cylinder which may be slidably moved axially along the syringe and relocated around the needle thereby covering and protecting the point.

The second category of devices developed for the avoidance of needle stick occurrences incorporate various mechanisms for retracting the needle into the hollow cylinder body after use.

The principle short-coming of the devices that assist the user in recapping or resheathing the needle is that the syringe is not rendered inoperable after use. Secondly, the caps are prone to be lost or fall off after recapping thereby becoming a later hazard to those subsequently handling the used syringe. Designs in this category include: U.S. Pats. to Pedicano, Pat. No. 4,610,667; Vennon, Pat. No. 4,596,562; and Sampson, Pat. Nos. 4,573,976 and 4,425,120.

The retracting needle devices likewise have significant short-comings. First, several of the designs, notably, U.S. Pats. to Haber, Pat. No. 4,710,170 and Jagger, Pat. No. 4,592,744, must be partially disassembled to be rendered safe. Disassembly is time consuming and potentially confusing for users. Additionally, the disassembled components may themselves be contaminated, defeating the objective of disassembly. An alternative category of retracting needle designs (as shown in U.S. Pat. to DeLuccia in FIGS. 5 and 6, Pat. No. 4,675,005) incorporates a threaded post on the fluid engaging face of the syringe piston to attach to a needle support or base structure and is supposedly designed to allow the needle base structure to detach from the syringe cylinder head by screwing the base structure into the cylinder head then reverse unscrewing the post from the base structure, thereby permitting the needle to be retracted along with the piston into the hollow cavity of the syringe cylinder. Unfortunately, for this later device, there is no effective means of determining whether the post will unscrew from the base structure or the base structure will unscrew from the cylinder, hence, this structure was apparently not found as satisfactory as one using a snap-in ring described in the same reference to hold the base structure in place while the post was withdrawn.

One of the primary short-comings of the existing retracting needle designs is that each requires use of a non-standard needle support structure. That is, a needle with a base that has to be specially manufactured as opposed to using standard parts. Non-standard components create problems of familiarity among users with the new syringe and lack of interchangeability with available needle configurations in addition to substantial added cost. Lack of familiarity increases the likelihood of accidents resulting from misuse and decreases likelihood of acceptance by users.

Lack of interchangeability precludes use of existing luer lock cannulas with the new syringes. For example, in the DeLuccia reference, the three embodiments shown each require a differently configured cannula or needle base, none of which include standard luer lock fittings.

Additionally, none of the retracting needle designs provide the dual capability of being used as a conventional syringe with a front mounting luer lock fitting available, should a user have a special requirement and conventional mounting is desired.

Not only is it desirable for a user to be able to both retract the needle of the syringe and thereafter make the syringe unreusable, but also, it is desirable that the same syringe be able to provide other features that make the concept suitable for a wide number of uses and under a variety of conditions. For example, it is desirable to make a device of this type that is usable not only as a syringe for delivering fluids or withdrawing fluids from a patient, but also usable in conjunction with a vacutainer, arterial catheter assembly, a spinal tap apparatus or any similar device having a hypodermic needle, in order to protect the health care provider while allowing access to fluid therein if so desired.

In addition, it is desirable for a syringe of this type that, when a plunger of the syringe is completely depressed, there is very little or virtually no air remaining in the interior of the syringe. This helps in assuring that air is not accidentally entrained with liquid being injected into a patient.

SUMMARY OF THE INVENTION

The present invention is usable in conjunction with a syringe, vacutainer or other medical apparatus wherein a needle is utilized to hypodermically inject fluid into or withdraw fluid from a patient. For example, a syringe is provided that includes a syringe barrel or cylinder surrounding an axially slidable and rotatable plunger having a mounting hub positioned on the fluid engaging end thereof. The syringe barrel also has a needle receiving end including an internal female threaded connection that is preferably a conventional female luer lock fitting.

A conventional needle having a support base that interferingly fits over the hub is received within the syringe barrel and is extendable through the luer lock fitting at the end of the syringe barrel by depression of the plunger. The needle support base includes a connector suitable for being threadably received in the female threaded connection for mounting the needle and associated base with respect to the barrel housing and this connector is preferably a radially extending flange or male luer lock fitting.

In order to place the needle in a usable configuration, the plunger is depressed and the needle is extended through the tip of the syringe barrel such that the needle support base engages the tip of the syringe barrel. The plunger is then rotated such that the male luer lock is threaded into the female luer lock so as to effectively lock the needle in position relative to the syringe barrel. The plunger is then withdrawn without rotation and the hub is frictionally disengaged from the needle support base such that the plunger can now reciprocate within the syringe barrel and the needle is in position to administer an injection or withdraw fluid from a patient. The needle is retracted by reversing this process.

An external female luer lock fitting is also provided at the tip of the syringe barrel. The external luer lock fitting allows the needle to be used in a conventional manner in a second operational configuration, if so desired.

OBJECTS OF THE INVENTION

Therefore, the objects of the present invention are: to provide a hypodermic needle apparatus including syringes and related devices utilizing a needle for transdermal penetration wherein the needle is retractable within a barrel of the apparatus subsequent to use without requiring to be touched by a health care provider manipulating the apparatus nor is the provider required to recap the bare needle after use, so as to inhibit accidental sticking of the provider by the needle; to provide such an apparatus utilizing a conventional needle having a standard base support and a luer lock type fitting; to provide such an apparatus wherein the needle is interferingly mounted upon a hub associated with a plunger of the apparatus when the needle is retracted within the barrel and which is held on the hub by friction and further that the needle is held by engagement of a luer lock fitting on the base of the needle with a mateable luer lock fitting within a top of the cylinder following the steps of depressing the plunger, rotating the plunger so as to mate the luer lock of the needle base support and of the barrel and thereafter axial withdrawing of the plunger so as to separate the hub from the needle base in a positive manner which ensures that the needle is securely locked in position relative to the barrel and which allows reversal of the process so as to retract the needle within the barrel; to provide such an apparatus wherein the plunger can be partially withdrawn from the barrel and medially broken without removal of the plunger from the barrel so as to render the apparatus unreusable, while positioning the needle fully within the cylinder so as to protect health care workers from possible stick by the needle; to provide such an apparatus that effectively combines the features of positive control over the retraction of the needle with the ability to render the apparatus unreusable; to provide such an apparatus that includes an external female luer lock fitting in addition to the previously described internal luer lock fitting such that the apparatus can be alternatively used in a conventional manner; to provide such an apparatus wherein the plunger and needle support base, when the plunger is fully depressed, generally fill the entire interior of the apparatus between the end of the plunger and the needle so as to substantially limit the amount of air within the apparatus; to provide such an apparatus wherein fluids may be withdrawn from within the apparatus, if so desired; to provide such an apparatus that is plugable subsequent to use and after withdrawal of the needle within the apparatus so as to prevent contamination by fluid seeping from the apparatus and to prevent the needle from being dislodged and protruding from the barrel; to provide such an apparatus that is disposable, relatively simple to use, inexpensive to manufacture, eliminates the need for a standard needle cover and is especially well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a syringe in accordance with the present invention, with portions broken away to show detail thereof.

FIG. 2 is a side elevational view of the syringe, showing an optional cover in phantom lines with portions broken away to show detail thereof and, further, showing the needle in a configuration allowing use thereof.

FIG. 3 is a side elevational view of the syringe showing the needle in a retracted position and showing a plunger of the syringe subsequent to being broken so as to render the syringe unreusable.

FIG. 4 is a fragmentary and enlarged side elevational view of the syringe, showing the needle in a ready-to-use configuration and with portions broken away to show detail thereof and, further, showing a support base for the needle mounted so as to be retractable into the syringe.

FIG. 5 is a fragmentary and enlarged side elevational view of the syringe, showing the needle mounted so as to be removable from the exterior of the syringe and with portions broken away to show detail thereof.

FIG. 6 is an enlarged, cross-sectional view of the syringe, taken along line 6—6 of FIG. 4.

DETAILED DESCRIPTION OF THE PREFERRED EMBODIMENT

Figure 7:
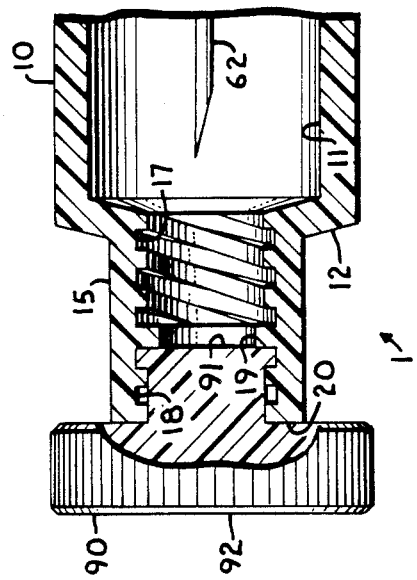
FIG. 7 is an enlarged and fragmentary view of the syringe with a plug positioned in the top thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally designates a syringe in accordance with the present invention. The syringe 1 includes a syringe barrel 5, a plunger 6 reciprocably mounted within the barrel 5 so as to be able to move axially and rotatably about the longitudinal axis thereof relative to the barrel 5 and a needle mechanism 7.

The syringe barrel 5 includes an elongate cylinder or tube 10 having an internal generally cylindrically shaped chamber 11 ending in a constricted neck or at least a partially enclosed tip 12 at one end 14 thereof. The plunger 6 reciprocably moves within the chamber 11. The syringe barrel end 14 receives the a needle mechanism 7 and has axially extending outwardly therefrom an integral support collar 15. The support collar 15 has an axially extending bore 16 passing therethrough and communicating with the barrel chamber 11.

The bore 16 has positioned therein connecting means, that in the illustrated embodiment included threaded structure including a first female luer lock fitting 17 and a second female luer lock fitting 18 separated by a stop 19. The first luer lock fitting 17 extends from the barrel chamber 11 to slightly less than halfway along the length of the bore 16. The luer lock fitting 18 extends from an exterior tip 20 of the collar 15 to slightly less than halfway along the bore 16, although it is foreseen that the stop 19 could be positioned along the bore 16 at many locations, including the tip 20. The luer lock fittings 17 and 18 include suitable luer lock connection threads that are substantially similar in shape and configuration except that fitting 18 extends from the collar tip 20 inward toward the stop 19 and fitting 17 extends from the chamber 11 outwardly toward the stop 19.

In the present embodiment, the stop 19 is a segment of the bore 16 having a slightly reduced radius, as measured from the central axis of the bore 16 and as compared to the remainder of the bore 16; however, it is foreseen that other stop means can be utilized. The stop 19 defines the limits of each of the luer lock fittings 17 and 18 and, as will be discussed below, prevents the needle mechanism 7 from passing through the stop 19 in either direction, as a portion of the needle mechanism 7 has a diameter larger than the diameter of the stop 19.

The barrel 5 includes on an end thereof opposite the support collar 15 a radially outwardly extending finger flange 25 adapted to receive pressure from fingers of an operator.

The plunger 6 includes an elongate piston 35 having a region 36 of reduced diameter immediately positioned therealong and thereby defining an area of weakness adapted for breaking by a user to render the syringe 1 unreusable. The plunger 6 may also include a second area of reduced diameter near the thumb plate 40 to allow a user greater control of the syringe 1. The plunger 6 has a first end 37 that is engageable with the needle mechanism 7, as discussed below, and which engages fluid within the barrel chamber 11. The plunger 6 includes a second end 38 axially and oppositely spaced from the first end 37. The second end 38 includes a thumb plate 40 adapted for engagement by a user during operation of the syringe 1.

Secured to the plunger first end 37 are sealing means such as the illustrated sealing mechanism 42. The sealing mechanism 42 effectively seals between the plunger 6 and the barrel chamber 11 as the plunger 6 reciprocates within the barrel chamber 11. It is foreseen that an O-ring positioned in a groove about the end of the plunger 6 could also function as a suitable sealing mechanism between the plunger 6 and barrel 5. The plunger first end 37 includes a face 45 that is directed toward the collar 15 and is shaped to fit snugly against an interior surface 46 of the syringe barrel tip 12, as seen in FIGS. 4 and 5.

Mounted so as to extend axially outward from the face 45 is a mounting pedestal 48. The mounting pedestal 48 has a diameter associated therewith which is sized so as to snugly fit within the bore 16 in the region of the first female luer lock fitting 17. The pedestal 48 is coaxially mounted relative to the plunger 6 and is secured to the plunger 6 so as to be movable both axially and rotationally with the plunger 6. When the needle mechanism 7 is mounted on the internal or first luer lock fitting 17, as described below, and the plunger 6 is fully depressed, the plunger 6 and especially the face 45 and exterior of the pedestal 48 generally fill the entire cavity 49 formed in the syringe 1 between the needle mechanism 7 and the plunger 6 except for a minimal space associated with the threads of the fitting 17 so as to effectively exclude substantially all air from the cavity 49 and reduce the possibility of air being injected inadvertently into a patient. It is foreseen that, in some embodiments, the fitting 17 may be replaced by a smooth wall for snugly receiving and supporting the needle base. In this manner, the pedestal 48 may closely fit against such a wall and virtually eliminate air from the interior of the syringe when the plunger 6 is fully depressed. It is also foreseen that a stylet or non-lumen rod may be mounted in the plunger 6 so as to extend through the needle mechanism 7 to eliminate all air therein also.

Extending further outwardly from the pedestal 48 is a needle mechanism mounting hub 50. The mounting hub 50 is preferably tapered away from the pedestal 48 and also positioned so as to be coaxial with the plunger 6 and to move both axially and rotationally with the plunger 6. The hub 50 is shaped like a smooth surfaced truncated cone with the widest portion thereof attached to the pedestal 48.

The needle mechanism 7 includes a support base 60 having an internal cavity 61, a needle 62 with a sharp tip or stylet extending axially outward from the base 60 and an internal lumen 63 passing through the needle 62 and flow communicating with the cavity 61. The support base 60 has an end 64 thereof opposite the needle 62 and includes thereon connecting means, such as the illustrated flange or male luer lock fitting 65, adapted to mate with the female luer lock fittings 17 and 18 in the collar 15. The fitting 65 includes a pair of radially outward extending flanges that are suitable for threadably mating with the fittings 17 or 18 alternatively. The needle mechanism 7 is a conventional needle mechanism and, consequently, the support base (especially the bottom thereof) is somewhat ovate in shape. Therefore, when the needle mechanism 7 is mounted, the stop 19 is positioned against alternatively the underside and the upperside of the luer lock fitting 65 depending upon whether the luer lock fitting 65 is threaded in the first female luer lock fitting 17 or the second female luer lock 18.

The male luer lock fitting 65 thus seals against the stop 19 when the needle mechanism 7 is in either of two operational configurations, the first configuration wherein the male luer lock fitting 65 is secured in the first female luer lock fitting 17 and the second when the male luer lock fitting 65 is secured in the second female luer lock fitting 18. When the male luer lock fitting 65 is secured in the first female luer lock fitting 17, as shown in FIG. 4, the hub 50 is positionable within the cavity 61 and, when so positioned, is snugly and interferingly received within the cavity 61. In particular, the cavity 61 is cone-shaped having a shape similar to or mateable with the exterior of the hub 50 with the cavity 61 being at least slightly longer than the hub 50 such that the hub 50 can be frictionally wedged into the cavity 61 so that the needle mechanism 7 is thereby rotatable by rotation of the plunger 6. In this manner, rotation of the plunger 6 and, consequently, the hub 50 in a counterclockwise manner when the plunger 6 is fully depressed, again as shown in FIG. 4, likewise causes rotation of the needle mechanism 7 in a counterclockwise direction and the male luer lock fitting 65 is unscrewed relative to the female luer lock fitting 17. Reversal of this process (that is, rotation of the plunger 6 in a clockwise rotation) screws the male luer lock fitting 65 into the female luer lock fitting 17 until the upper side of the fitting 17 is snug against and seals against the stop 19. When this point is reached, axial withdrawal of the plunger 6, in a direction opposite from that of the needle mechanism 7, frictionally draws the hub 50 from the chamber 61 thereby leaving the needle mechanism 7 in the first operational configuration thereof and allowing the plunger 6 to operate reciprocably within the chamber 11 independent from the needle mechanism 7.

FIG. 5 illustrates mounting of the needle mechanism 7 from the outside of the bore 16. That is, the male luer lock fitting 65 is threaded by clockwise rotation thereof into the female luer lock fitting 18 until snug against the stop 19 at which time the needle mechanism 7 is mounted in a second operational configuration thereof. The needle mechanism 7 is thereafter removable from the remainder of the syringe 1 by counterclockwise rotation of the needle mechanism 7 about its axis so as to unscrew the male luer lock fitting 65 from the female luer lock fitting 18.

A protective cap 70 such as illustrated by the phantom lines in FIG. 2 may be placed over the needle mechanism 7 at any time the needle 62 is exposed outside of the chamber 11 and especially when mounted in the configuration shown in FIG. 5.

Shown in FIG. 7 is a plug 90 that includes a threaded portion 91 and a cap portion 92. The threaded portion 91 may selectively be screwed into the threaded luer lock fitting 18 and is sealably mateable therewith when the needle mechanism 7 is withdrawn into the barrel 5 to prevent seepage out of the interior of the syringe 1 and to prevent the needle 62 from being dislodged and sticking through the end of the collar 15.

Figure 8:
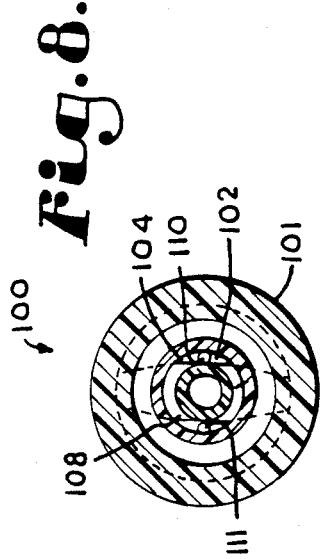
FIG. 8 is a cross-sectional view of a first modified syringe according to the present invention, showing detail of pins mounted on a hub to prevent rotation of a needle base support associated therewith during mounting of the needle base support into a ready-to-use configuration.
Figure 9:
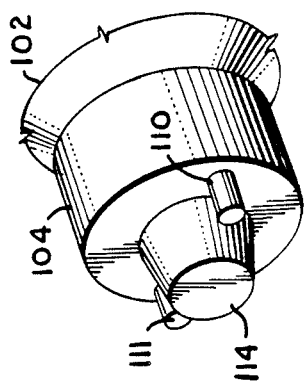
FIG. 9 is an enlarged and fragmentary perspective view of the first modified syringe with portions broken away to show detail thereof.

Shown in FIGS. 8 and 9 is a modified embodiment of a syringe 100 in accordance with the present invention. The syringe 100 is quite similar to the syringe 1 and, therefore, similar features of the two syringes will not be redescribed in detail.

The syringe 100 includes a barrel 101 having mounted reciprocably therein a plunger 102 and a needle mechanism 103. Mounted on the end of the plunger 102 nearest the needle mechanism 103 is a pedestal 104 which interferingly engages a mounting base 108 of the needle mechanism 103. The base 108 is ovate in shape.

The major difference between the syringe 100 and the syringe 1 is that a pair of ears, wings or posts 110 and 111 are fixedly secured to the pedestal 104 between a needle base engaging hub 114. The posts 110 and 111 are positioned so as to extend outwardly from the pedestal 104 in the direction of the needle mechanism 103 parallel to the axis of the plunger 102. The posts 110 and 111 are also positioned so as to be spaced approximately the same distance as the width of the needle mechanism support base 108, as shown in FIG. 7. In this manner, when the plunger 102 is fully depressed, the posts 110 and 111 are positioned on opposite sides of the base 108, such that when the plunger 102 is rotated, the posts 110 and 111 interferingly engage the base 108 to positively assure rotation of the base 108 with the posts 110 and 111 and, consequently, with the plunger 102.

Although the present invention has been described specifically in conjunction with the use of a syringe of a particular type, it is foreseen that the present invention can be utilized in conjunction with a wide variety of syringes, vacutainers, spinal taps and virtually any medical instrument wherein a needle is utilized to puncture the skin of a patient in order to either inject fluids into the patient or withdraw fluids from the patient.

It is foreseen that the present invention may also be utilized in an arterial catheter assembly wherein a needle (trocar or stylet) of the assembly is mounted as the needle in FIG. 4 and removable by use of a plunger mechanism similar to the plunger of FIG. 4 with the difference being that a catheter or cannula is shrouded on the needle and is mounted in an outer luer lock fitting with the needle extending from the cannula when the plunger is depressed. In this manner, the tip of the needle can be utilized to produce a path for the cannula and then the plunger can be withdrawn to draw the needle out leaving the cannula in the patient and attached to a barrel of the assembly. At that time, a penetratable seal of rubber or the like can be positioned over the rear of the barrel to allow a syringe needle or the like to be passed through the seal to sample fluids in the barrel or withdraw fluids from the barrel. The seal may also be joined to tubing for infusion of fluids, monitoring of pressure or the like.

It is also foreseen that the present invention may be utilized in a glass syringe by sealably mounting a collar such as described in the previous embodiment in the nozzle or tip of a barrel of the syringe.

It is to be understood that while certain forms of the present invention have been illustrated and described herein, it is not to be limited to the specific forms or arrangement of parts described and shown.

What is claimed and desired to be secured by Letters Patent is as follow:

1. In a hypodermic needle apparatus having a needle for puncturing the skin of a patient and including a barrel for supporting the needle during use; the improvement comprising:
   (a) said barrel having a collar at one end thereof with a bore passing through said collar and having a first internal threaded connection means within said bore;
   (b) said first connection means being accessible from within said barrel;
   (c) a needle mechanism including said needle and a support base; said support base having an axially aligned internal cavity opposite said needle and second threaded connection means mateable with said first connection means; said cavity having a generally smooth conically shaped surface extending to the exterior of the support base; and
   (d) a plunger reciprocably mounted within said barrel; said plunger having mounted thereon a hub extending axially outward toward said needle base; said hub having an outer surface having generally the shape of a smooth truncated cone that is sized to be frictionally received in said cavity; said hub being axially aligned with said cavity, wherein said hub is snugly positioned in said cavity by depression of said plunger, said hub frictionally engages said cavity and casuses said needle mechanism to rotate upon rotation of said plunger and so as to allow disengagement of said plunger from said needle mechanism, when said first connection means is separated from said second connection means by axial withdrawal of said plunger.

2. In a hypodermic needle apparatus including a barrel and a needle supported by said barrel; the improvement comprising:
   (a) said barrel having a collar at one end thereof; said collar having an internal bore;
   (b) said bore having first connection means associated therewith accessible from within said barrel; said first connection means allowing a support base to be mounted thereon from within said barrel; and
   (c) said bore having second externally accessible connection means associated therewith opposite said first connection means and separated therefrom by a stop; said second connection means allowing a needle base to be alternatively mounted therein from outside of said apparatus.

3. The apparatus according to claim 2 wherein:
   (a) said first and second connection means each comprise female threaded fittings sized to receive a common male fitting mounted on said needle base.

4. The apparatus according to claim 3 wherein: (a) said male fitting comprises a pair of flanges; and (b) said needle base is a conventional needle base with an ovate shape with said pair of flanges radially extending outward therefrom.

5. The apparatus according to claim 2 wherein: (a) said support base is secured to a catheter; and (b) said needle base is secured to a needle receivable within said catheter and extending slightly beyond said catheter when fully received in said catheter.

6. The apparatus according to claim 2 wherein: (a) said support base and said needle base are a single base attached to said needle such that said needle may be selectively mounted from inside or alternatively from outside of said apparatus into said collar.

7. In a hypodermic needle apparatus having a needle for puncturing the skin of a patient and including a barrel for supporting the needle during use; the improvement comprising:
   (a) said barrel having a collar at one end thereof with a bore passing through said collar and having a first internal threaded connection means within said bore;
   (b) said first connection means being accessible from within said barrel;
   (c) a needle mechanism including said needle and a support base; said support base having an axially aligned internal cavity opposite said needle and second threaded connection means mateable with said first connection means;
   (d) a plunger reciprocably mounted within said barrel; said plunger having mounted thereon a hub extending axially outward toward said needle base; said hub sized and shaped so as to interferingly mate with said base cavity when said hub is urged into said cavity by depression of said plunger so as to allow rotation of said needle mechanism by rotation of said plunger, when mated, and so as to allow disengagement of said plunger from said needle mechanism, when said first connection means is separated from said second connection means by axial withdrawal of said plunger;
   (e) said collar includes third threaded connection means positioned to extend along said bore opposite said first connection means and being mateable with said second connection means on said needle base; and including:
   (f) a stop positioned between said first and third connection means such that said needle base can be mounted from the exterior of said apparatus into said collar by the mating of said second and third connection means and alternatively can be mounted in said collar from the interior of said barrel by the mating of said first and second connection means.

8. The apparatus as called for in claim 7 wherein:
(a) said needle mechanism is a standard needle mechanism having an ovate base and wherein said second connection means is a standard male luer lock fitting.

9. The apparatus as called for in claim 7 including:
(a) a plug having fourth threaded connection means mateable with said third connection means; said plug being positionable within said collar and secured therein by mating of said third and fourth connection means so as to plug said bore.

10. In a hypodermic needle apparatus having a needle for puncturing the skin of a patient and including a barrel for supporting the needle during use; the improvement comprising;
(a) said barrel having a collar at one end thereof with a bore passing through said collar and having a first internal threaded connection means within said bore;
(b) said first connection means being accessible from with said barrel;
(c) a needle mechanism including said needle and a support base; said support base having an axially aligned internal cavity opposite said needle and second threaded connection means mateable with said first connection means;
(d) a plunger reciprocably mounted within said barrel; said plunger having mounted thereon a hub extending axially outward toward said needle base; said hub sized and shaped so as to interferingly mate with said base cavity when said hub is urged into said cavity by depression of said plunger so as to allow rotation of said needle mechanism by rotation of said plunger, when mated, and so as to allow disengagement of said plunger from said needle mechanism, when said first connection means is separated from said second connection means by axial withdrawal of said plunger; and
(e) said plunger has extending axially therefrom a pin positioned so as to be located beside said needle base when said hub is in said cavity such that said pin engages and positively rotates said base upon rotation of said plunger.

11. In a hypodermic needle apparatus including a barrel and a needle supported by said barrel; the improvement comprising:
(a) said barrel having a collar at one end thereof; said collar having an internal bore;
(b) said bore having first connection means associated therewith accessible from within said barrel; said first connection means allowing a support base to be mounted thereon from within said barrel;
(c) said bore having second externally accessible connection means associated therewith; said second connection means allowing a needle base to be selectively mounted therein from outside of said apparatus; and wherein:
(d) said first and second connection means each comprise female threaded fittings sized to receive a common male fitting mounted on said needle base; and including:
(e) stop means positioned between said first and second connection means and sized to prevent said male fitting from passing through said bore past said stop means in either direction.

* * * * *